US008718291B2

(12) United States Patent
Alves et al.

(10) Patent No.: US 8,718,291 B2
(45) Date of Patent: May 6, 2014

(54) ANC FOR BT HEADPHONES

(75) Inventors: Rogerio Guedes Alves, Macomb Township, MI (US); Walter Zuluaga, Rochester Hills, MI (US)

(73) Assignee: Cambridge Silicon Radio Limited, Cambridge (GB)

( * ) Notice: Subject to any disclaimer, the term of this patent is extended or adjusted under 35 U.S.C. 154(b) by 501 days.

(21) Appl. No.: 12/984,941

(22) Filed: Jan. 5, 2011

(65) Prior Publication Data

US 2012/0170766 A1 Jul. 5, 2012

(51) Int. Cl.
*A61F 11/06* (2006.01)

(52) U.S. Cl.
USPC ........................................ 381/71.11; 381/71.8

(58) Field of Classification Search
USPC ................ 381/71.1, 71.6, 71.8, 71.11, 71.12, 381/94.1; 708/3, 300, 313, 405
See application file for complete search history.

(56) References Cited

U.S. PATENT DOCUMENTS

| | | | | |
|---|---|---|---|---|
| 4,455,675 | A | 6/1984 | Bose et al. | |
| 5,241,679 | A | 8/1993 | Nakagawa et al. | |
| 6,449,369 | B1 | 9/2002 | Carme et al. | |
| 2004/0264706 | A1* | 12/2004 | Ray et al. | 381/71.11 |
| 2008/0310645 | A1 | 12/2008 | Itabashi et al. | |
| 2010/0195844 | A1 | 8/2010 | Christoph et al. | |
| 2010/0296668 | A1 | 11/2010 | Lee et al. | |
| 2011/0007907 | A1* | 1/2011 | Park et al. | 381/71.8 |

FOREIGN PATENT DOCUMENTS

| | | | |
|---|---|---|---|
| EP | 1638079 | A2 | 3/2006 |
| GB | 2441835 | A | 3/2008 |
| WO | WO 03/005581 | A1 | 1/2003 |
| WO | 2010/014663 | A2 | 2/2010 |
| WO | 2011/006148 | A1 | 1/2011 |

OTHER PUBLICATIONS

B.C. Kuo and F. Golnaraghi, "Automatic Control Systems", 7th Ed., Prentice Hall NJ, 1995, pp. 1-19, 664-671.
S. Elliott, "Signal Processing for Active Control", Academic Press 2001, pp. 105-106, 132-133, 154-155, 335-338.
S.M. Kuo and D.R. Morgan, "Active Noise Control Systems, Algorithms and DSP Implementations", John Wiley and Sons, Inc. 1996, pp. 48-49, 62-65, 195-199.
M. Akhtar and W. Mitsushashi, Hybrid Active Noise Control System for Correlated and Uncorrelated Noise Sources, *Proc. 6th Int'l Symp. on Image and Signal Processing and Analysis*, pp. 17-21, 2009.
K.C. Zangi, A New Two-Sensor Active Noise Cancellation Algorithm, *IEEE*, pp. II-351-II-354 1993.

(Continued)

*Primary Examiner* — Vivian Chin
*Assistant Examiner* — Friedrich W Fahnert
(74) *Attorney, Agent, or Firm* — Frommer Lawrence & Haug LLP; John W. Branch

(57) ABSTRACT

An active noise cancellation controller for performing noise attenuation in a system over a predetermined frequency rang. The controller comprises several components: a first input for a reference signal indicative of a noise level; a second input for receiving an error signal indicative of a remnant noise level; an output for providing a noise cancellation signal; a fixed feedback controller for processing the error signal; a fixed feed-forward controller for processing the reference signal; and an adaptive feed-forward controller having a digital adaptive finite impulse response filter arranged for operation on the reference signal the error signal.

20 Claims, 12 Drawing Sheets

(56) References Cited

OTHER PUBLICATIONS

A. Streeter, L. Ray and R. Collier, "Hybrid Feedforward-Feedback Active Noise Control," *Proc. American Control Conference*, pp. 2876-2881, Jun.-Jul. 2004.
Y. Song and S. Kuo, "A Robust Hybrid Feedback Active Noise Cancellation Headset," *IEEE Trans. Speech and Audio Processing*, vol. 13, No. 4, pp. 607-617, Jul. 2005.
D. Morgan and J. Thi, "A Delayless Subband Adaptive Filter Architecture," *IEEE Trans. Signal Processing*, vol. 43, No. 8, pp. 1819-1830, Aug. 1995.
R. Alves, M. Petraglia and P. Diniz, "Convergence Analysis of an Oversampled Subband Adaptive Filtering Structure Using Global Error," *IEEE*, pp. 468-471, 2000.
S. Yu and J. Hu, "Controller Design for Active Noise Cancellation Headphones Using Experimental Raw data," *IEEE Trans. Mechatronics*, vol. 6, No. 4, pp. 483-490 Dec. 2001.
S. Kuo and D. Morgan, "Active Noise Control: A Tutorial Review," *Proc. IEEE*, vol. 87, No. 6, pp. 943-973, Jun. 1999.
S. Kuo, S. Mitra and W. Gan, Active Noise Control for Headphone Applications, *IEEE Trans. Control Systems Technology*, vol. 14, No. 2, pp. 331-335, Mar. 2006.
B. Rafaely, "Feedback Control of Sound," Doctor of Philosophy thesis, Univ. of Southampton, UK, Oct. 1997.
Product Info. for BlueCore® 5-Multimedia Flash, Single Chip Bluetooth® v2.1 + EDR System, Cambridge Silicon Radio Ltd. 2007-2008.
User's Manual for Noise Canceling Headphones, MDR-NC500D, Sony Corp. 2008.
Akhtar et al, "Hybrid Active Noise Control System for Correlated and Uncorrelated Noise Sources", Proceedings of the 6$^{th}$ International Symposium on Image and Signal Processing and Analysis, Sep. 16-18, 2009, pp. 17-21, ISBN 978-953-184-135-1, Salzburg, Austria.
UK Intellectual Property Office Search Report for Application No. GB1200115.2, dated Apr. 16, 2012.
B.C Kuo and F. Golnaraghi, Automatic Control Systems:, 7th Ed., Prentice Hall, NJ, 1995, pp. 10-11, 489-491, and 588-589.
S. Elliott, "Signal Processing for Active Control," Academic Press 2001, pp. 105-106, 132-133, 154-155 and 335-338.
S.M. Kuo and D.R. Morgan, "Active Noise Control Systems, Algorithms and DSP Implementations", John Wiley and Sons, Inc., 1996, pp. 62-65, 48-49, and 195-199.
P.S.R. Diniz, "Adaptive Filtering: Algorithms and Practical Implementation," Prentice Hall, 1991, pp. 376-378.
Translation of Examination Report issued in German Patent Application No. 102012200142.5, mailed on Jan. 7, 2014.

* cited by examiner

ANC FOR BT HEADPHONES

FIELD OF THE DISCLOSURE

This disclosure relates to a hybrid active noise cancellation controller for implementation at an integrated circuit.

BACKGROUND

Active noise cancellation (ANC) technology has been developing for many years and a range of headphones incorporating ANC technology (also known as ambient noise reduction and acoustic noise cancelling headphones) are now available on the market. ANC headphones are however often larger, heavier and require a dedicated power source in comparison to equivalent headphones that do not provide ANC functionality. Such characteristics are generally viewed negatively by consumers who generally want headphones to be small, light and the power source to last as long as possible. There is therefore a general desire to continue to reduce the size, weight and power requirements of ANC headphones whilst maintaining noise cancellation performance.

There has also been a growth in recent years in the use of wireless headphones, such as Bluetooth headphones that support an A2DP profile. Wireless headphones require circuitry to support the wireless reception of audio data and a battery to power that circuitry. Wireless headphones are therefore also generally bulkier and heavier than equivalent wired headphones and require regular recharging.

It would be desirable to offer ANC functionality in wireless headphones but using conventional technologies this would require adding additional circuitry providing the ANC functionality to wireless headphones, further increasing their size, weight and power requirements. There is therefore a need for a low-power ANC solution that can be readily incorporated in wireless headphones without significantly increasing the size and weight of the headphones.

In particular, there is a desire to incorporate ANC functionality into the wireless communication controller present in wireless headphones. And given the recent growth in the sales of Bluetooth headphones, there is a particular desire to incorporate ANC functionality into a Bluetooth controller. However, communication controllers generally do not have the characteristics suitable for implementing conventional ANC controller—typically there will be excessive delays on the digital path and low computational processing power. There is therefore a need for an ANC controller that can be implemented with low computational complexity and can operate at a processor or communications controller having significant delays on its digital path.

The central idea of ambient noise reduction headphones is illustrated in FIG. 1, in which a microphone 101 is used to capture ambient noise Ni(t) inside of the ear cup 100 that is present as a result of noise Ne(t) in the environment of the headphones. An anti-noise signal is produced by a loudspeaker 102 that has the same amplitude but opposite phase to the captured ambient noise so as to cancel out the ambient noise Ni(t) in the ear cup. e(t) is the signal captured by microphone, −c(t) is the ANC controller, and u(t) is the noise cancellation signal provided by the controller to the speaker.

Active noise cancellation can be equated to the disturbance rejection problem from control system theory, which is shown in FIG. 2 and described in "Automatic Control Systems", $7^{th}$ Ed. by B. C. Kuo and F. Golnaraghi, Prentice Hall, N.J., 1995. Comparing FIG. 2 with the headphones illustration in FIG. 1, the error signal e(t) is the signal captured by microphone 101, the controller −C(s) maps onto controller −c(t) of the noise reduction headphones (the minus signal indicates a negative feedback system), the plant P(s) is the transfer function from the input of the loudspeaker to the output of the microphone 101, and the disturbance d(t) in FIG. 2 is the ambient noise inside of the ear cup, Ni(t) in FIG. 1.

Observe that the error signal output e(t) of the control system in FIG. 2 will, in the absence of the control, be equal to d(t) or Ni(t)—i.e. no noise attenuation is achieved. The transfer function (or sensitivity function) from the disturbance signal to the error signal can be obtained, $$\frac{E(s)}{D(s)} = \frac{1}{1 + P(s) \cdot C(s)} = S(s)$$

Since the objective of this control system is good rejection of the disturbances, S(s) should be small, $$|1+P(s).C(s)| \gg 1$$

An appropriate controller function C(s) can therefore be designed by measuring plant P(s) (it is the transfer function from the input of the loudspeaker 102 to the output of the microphone 101). This kind of controller is known as a feedback (FB) controller and its analog version, which can be designed using control theory, is suitable for use in the ANC controllers of headphones.

Broadly, there are two different arrangements used in commercial ambient noise reduction headphones: the feedback (FB) arrangement that uses a microphone 302 inside of the ear cup 301 as shown in FIG. 3A, and the feedforward (FF) arrangement that uses a microphone 303 outside of the ear cup 304 as shown in FIG. 3B. Generally, headphones with large ear cups use an FB arrangement and ear bud style headphones use the more compact FF arrangement (which does not require a microphone between the headphone speaker and the user's ear).

ANC controllers for either arrangement can be analog or digital, and fixed or adaptive. Historically, most commercial ambient noise reduction headphones have used analog, fixed controllers because digital controllers that offer sufficiently low delay characteristics to be useful as a digital ANC controller have been expensive and power hungry. For example, U.S. Pat. No. 4,455,675, describes a fixed analog feedback controller for ANC headphones.

More recently, digital controllers have become prevalent, such as the fixed digital controller described in U.S. patent application Ser. No. 2008/0310645 that can switch among three modes (feedback, feedforward and a hybrid feedback-feedforward mode) in dependence on the environmental noise characteristics. Sony Corporation have also released a pair of noise cancelling headphones that use a feedback digital controller and microphone arrangement—model MDR-NC500D.

Adaptive digital ANC controllers will now be considered that employ adaptive algorithms, such as least mean squares (LMS) or recursive least squares (RLS) algorithms. Most preferably the adaptive controller is configured to operate in accordance with an FXLMS (Filtered-Reference Least Mean Squares) algorithm, such as the algorithm described in "Signal Processing for Active Control" by S. Elliott, Academic Press, 2001, and in "Active Noise Control Systems, Algorithms and DSP Implementations" by S. M. Kuo and D. R. Morgan, John Wiley and Sons, 1996.

FIG. 4 is a block diagram of a control system representing an adaptive feedback ANC controller that uses the FXLMS adaptive algorithm with an adaptive filter and is suitable for use in the feedback arrangement shown in FIG. 3A. Signal Ni(k) represents the ambient noise inside the ear cup 301, e(k) is the error signal generated by the internal microphone 302, x(k) is the "generated" reference signal, and u(k) is the output of the adaptive filter −C(k). Typically adaptive filter −C(k) is an FIR (finite impulse response) filter whose coefficients are set in accordance with the FXLMS algorithm. P(z) represents the plant model transfer function from the input of the loudspeaker 303 to the output of the microphone 302—this can be measured from a real-world system.

Theoretical simulations of the controller can be performed once the plant transfer function P(z) of the real-world system being modeled has been measured (the plant transfer function being a mathematical representation of the convolved frequency responses of the loudspeaker and microphone, the acoustic path between loudspeaker and microphone and the characteristics of the electronics coupled to the microphone and loudspeaker). The convolution of plant P(z) with the loudspeaker input signal (u(k)) and the superposition of the convolution result with the ambient noise signal Ni(k) represents the response of the real-world system to the ambient noise signal that naturally occurs inside the ear cup of the headphones. Simulations of an ANC controller can be performed in numerical computing packages, such as MATLAB.

The objective of the adaptive controller is to adjust the coefficients of adaptive filter −C(k) in order to minimize error signal e(k). Adaptive algorithm FXLMS is used to achieve this end. The behavior of the controller shown in FIG. 4 can be described by the following set of equations. Firstly, we define e(k), $$e(k)=n_i(k)+P^T(k)\cdot U(k)$$

where P(k) and U(k) are column vectors with length M, $$P(k)=[p_1(k)p_2(k)\ldots p_M(k)]^T$$

$$U(k)=[u_1(k)u_2(k-1)\ldots u_M(k-M+1)]^T$$

Secondly, we define how the coefficients of the adaptive filter C(k) are updated so as to minimize the error e(k):

$$C(k+1)=C(k)-\mu.\hat{X}(k).e(k)$$

where μ is the step size of the LMS algorithm and C(k) and $\hat{X}(k)$ are column vectors given by:

$$C(k)=[c_1(k)c_2(k)\ldots c_N(k)]^T$$

$$\hat{X}(k)=[\hat{x}(k)\hat{x}(k-1)\ldots\hat{x}(k-N+1)]^T$$

with N representing the number of coefficients of C(k).

u(k), x(k) and $\hat{x}(k)$ are given by:

$$u(k)=X^T(k).C(k)$$

$$x(k)=e(k)+\hat{P}^T(k).U(k)$$

$$\hat{x}(k)=\hat{P}^T(k).X(k)$$

with X(k) a column vector given by:

$$X(k)=[x(k)x(k-1)\ldots x(k-N+1)]^T$$

Generally, to simplify the algorithm it is assumed that $\hat{P}(z)=P(z)$. Algorithms other than FXLMS can be used, and several alternatives are described in the "Signal Processing for Active Control" and "Active Noise Control Systems, Algorithms and DSP Implementations" textbooks referenced above.

A feedforward adaptive controller will now be considered, which is also described in the "Signal Processing for Active Control" and "Active Noise Control Systems, Algorithms and DSP Implementations" textbooks. As illustrated in FIG. 5, for a feedforward adaptive controller, two microphones 501, 502 are generally necessary for each ear cup 500 of the headphones: an internal microphone 502 and an external microphone 501.

FIG. 6 is a block diagram of a control system representing an adaptive feedforward controller suitable for implementation at the headphones of FIG. 5. The main difference compared to the feedback system is that the reference signal x(k) is now provided by signal Ne(k) from the external microphone 501. FIG. 6 identifies a transfer function 601 between the internal and external microphones H(z), with the goal of the adaptive algorithm being to find a controller given by, $$C(z)=-H(z)*P(z)^{-1}$$

The equations describing the feedforward adaptive controller can be obtained from the equations describing the feedback adaptive controller by realizing that x(k) is equal to the signal from the external microphone. The internal microphone 502 is not shown in FIG. 6 because its presence is represented by e(k).

Again, the plant model P(z) can be obtained by measurement of the headphone system, which, for a digital system, typically includes: a digital to analog converter (DAC); an analog to digital converter (ADC); a DAC reconstruction low-pass filter; an ADC anti-aliasing low-pass filter; loudspeaker and microphone amplifiers; the acoustic path between loudspeaker and microphone; and the microphone and loudspeaker impulse responses.

A third variant of ANC controller is the hybrid feedforward-feedback controller. The combination of the feedforward and feedback type of controllers can achieve higher active noise attenuation than each controller type alone. Hybrid feedforward-feedback controllers are described in detail in "A New Two-Sensor Active Noise Cancellation Algorithm", Proc. of the International Conference on Acoustic, Speed and Signal Processing, 1993; "Hybrid Feedforward-Feedback Active Control", Proc. of the American Control Conference, Boston, 2004; and "Hybrid Active Noise Control System for Correlated and Uncorrelated Noise Sources", Proc. of the $6^{th}$ International Symposium on Image and Signal Processing and Analysis, 2009.

A schematic diagram of headphones implementing a hybrid feedforward-feedback controller are shown in FIG. 7. The headphones comprise internal and external microphones 701 and 702, respectively, within each headphone cup 700. The arrangement of the feedback and feedforward filters with respect to the inputs from the microphones and the output to the loudspeaker is shown in the figure.

An adaptive hybrid feedforward-feedback controller embodying the FXLMS adaptive algorithm is presented as a control system in FIG. 8. Both the feedback controller C_fb (k) and the feedforward controller C_ff(k) are adaptive filters whose coefficients are determined in accordance with the FXLMS algorithm. The aggregate controller arrangement can be seen to be a combination of the feedback controller shown in FIG. 4 and the feedforward controller shown in FIG. 6.

ANC controllers can be either analog or digital. For digital controllers, the delay on the digital path (which forms part of the plant model) is critical to the performance of the controller. Typically, the main contribution to the delay is from the digital signal processor (DSP). If the digital path presents a large delay, the controller will not be able to cancel a broadband signal but it can still cancel periodic signals, such as tones of fixed frequency. Such considerations led to the development of feedback hybrid analog-digital controllers, which use an analog fixed feedback controller and a digital adaptive feedback controller. Examples of this type of controller are set out in "Feedback control sound", a PhD thesis by B. Rafael of University of Southampton, 1997, and in "A Robust Hybrid Feedback Active Noise Cancellation Headset" by Y. Song et al., IEEE Trans. On Speech and Audio Processing, Vol. 11, No. 4, Jul. 2005. These controllers can handle both broadband input signals and periodic input signals, with an analog controller being used to attenuate the broadband signals (analog filters having a short delay can be readily constructed) and a digital controller being used to attenuate the periodic input signals.

FIG. 9 shows a block diagram of the general structure of a typical feedback hybrid analog-digital controller. A microphone 101 and a loudspeaker 102 are configured at a pair of headphones as shown in FIG. 1. The signal from the microphone is amplified at pre-amp 903 to form error signal e(k), which is provided to both the analog signal path and analog controller 908, and to the digital signal path. The digital signal path comprises an anti-aliasing low-pass filter 904, an analog-to-digital controller (ADC) 907, DSP digital controller 906, digital-to-analog controller (DAC) 905 and reconstruction low-pass filter 901. The signals from the digital and analog paths are combined at 909 and provided to a power-amp 902 that drives loudspeaker 102.

Various types of conventional ANC controller have been described above. However, none of these basic controller types provide an efficient, low-complexity solution that offers excellent ANC performance yet is suitable for incorporation at a low power processor or communication controller that may include a significant delay on the digital path.

SUMMARY

According to a first aspect of the present disclosure there is provided an active noise cancellation controller for performing noise attenuation in a system over a predetermined frequency range, the active noise cancellation controller comprising: a first input for receiving a reference signal indicative of a noise level; a second input for receiving an error signal indicative of a remnant noise level; an output for providing a noise cancellation signal to a system in which noise attenuation is to be performed; a fixed feedback controller having a fixed infinite impulse response filter arranged for operation on an error signal received at the second input; a fixed feedforward controller having a fixed infinite impulse response filter arranged for operation on a reference signal received at the first input; and an adaptive feedforward controller having a digital adaptive finite impulse response filter arranged for operation on a reference signal received at the first input and on an error signal received at the second input, the coefficients of the digital adaptive filter being determined by: in the frequency domain, independently generating a set of initial coefficients for each of a plurality of subbands into which the predetermined frequency range is divided, said sets of initial coefficients being generated in accordance with a predetermined adaptive algorithm; and transforming said sets of initial coefficients into the time domain for use as the said coefficients of the digital adaptive filter; wherein the fixed feedback controller, fixed feedforward controller and adaptive feedforward controller are arranged to, in use, provide a noise cancellation signal at the output in dependence on a reference signal received at the first input and an error signal received at the second input.

The adaptive feedforward controller preferably further comprises: a first Discrete Fourier Transform unit operable to form a frequency domain representation of a reference signal received at the first input; and a second Discrete Fourier Transform unit operable to form a frequency domain representation of an error signal received at the second input; wherein the predetermined adaptive algorithm is configured to generate the initial coefficients using frequency domain representations of error and reference signals so formed at the first and second Discrete Fourier Transform units.

Preferably, the first and second Discrete Fourier Transform units are configured to, on forming a frequency domain representation, generate a set of parameters for each subband of the predetermined frequency range, the parameters of a subband being frequency domain representations of the error and reference signals in that subband.

Preferably, the adaptive feedforward controller further comprises a third Discrete Fourier Transform unit operable to transform initial coefficients generated by the predetermined adaptive algorithm into the time domain for use as the said coefficients of the digital adaptive filter.

Preferably, the third Discrete Fourier Transform unit is configured to use an inverse Fast Fourier Transform algorithm.

Preferably, the adaptive feedforward controller further comprises a coefficient mapping unit configured to, for each subband: form an estimate of the magnitude of an error signal at the second input in the subband due to the fixed feedback and fixed feedforward controllers but not due to the adaptive feedforward controller; and if the estimate of the magnitude of the error signal at the second input in the subband is greater than the magnitude of an error signal at the second input due to the fixed feedback and fixed feedforward controllers and the adaptive feedforward controller: provide the set of initial coefficients of the subband to the third Discrete Fourier Transform unit for conversion into the time domain; and otherwise: set the initial coefficients of the subband to zero and provide the zeroed initial coefficients to the third Discrete Fourier Transform unit.

Preferably, the adaptive feedforward controller is configured to, for each subband and from a reference signal received at the first input, form said estimate of the magnitude of an error signal at the second input in the subband due to the fixed feedback and fixed feedforward controllers in dependence on, firstly, a stored transfer function that relates a reference signal received at the first input to an error signal received at the second input and, secondly, a stored plant function that relates a combined output of the fixed feedback and fixed feedforward controllers to an error signal received at the second input, the transfer function and plant function being mathematical representations of a physical system in which the active noise cancellation controller is configured to perform noise attenuation.

Preferably, the active noise cancellation controller further comprises first and second decimation units and an interpolation unit: the first decimation unit being arranged to operate on a reference signal received at the first input and the second decimation unit being arranged to operate on an error signal received at the second input, the decimation units being configured so as to reduce the effective sampling rate of the respective signals by a predetermined factor and provide the decimated signals to the first and second Discrete Fourier Transform units; and the interpolation unit being arranged to operate on the cancellation signal generated by the adaptive feedforward controller so as to increase the effective sampling rate of the cancellation signal by said predetermined factor.

Suitably, the active noise cancellation controller is adapted for use at an audio device such that: the first input is configured to receive a reference signal from a first microphone, the reference signal being representative of the level of acoustic noise in the environment of the headphones or audio headset;

the second input is configured to receive an error signal from a second microphone, the error signal being representative of the level of acoustic noise remaining at the second microphone as a result of the operation of the active noise cancellation controller; and the output of the active noise cancellation controller is configured to provide a noise cancellation signal to a loudspeaker so as to cause the loudspeaker to perform acoustic noise cancellation at the second microphone.

Suitably, the audio device is a pair of headphones or an audio headset. Preferably, the first microphone is located on the exterior of the pair of headphones or audio headset and the second microphone is located substantially between the loudspeaker and an audio port adapted for engagement with a human ear and arranged to, in use, convey acoustic signals generated at the loudspeaker to a human ear so engaged.

The predetermined adaptive algorithm could be a least mean squares (LMS) or recursive least squares (RLS) algorithm, and is preferably a Filtered-Reference Least Mean Squares algorithm.

Preferably, the subbands cover collectively in frequency the predetermined frequency range. Preferably, the frequency range of each subband is significantly less than the predetermined frequency range. Preferably, the frequency range of each subband is at least one order of magnitude less than the predetermined frequency range, and is preferably 40 times less than the predetermined frequency range. Suitably, the predetermined frequency range is approximately 1000 Hz and the frequency range of each subband is approximately 25 Hz. Preferably, adjacent subbands do not overlap in frequency.

Preferably, the fixed infinite impulse response filters of the fixed feedback controller and the fixed feedforward controller are digital filters.

According to a second aspect of the present disclosure there is provided an integrated circuit comprising a wireless communications controller and an active noise cancellation controller as claimed in any preceding claim. Suitably, the wireless communications controller is a Bluetooth controller.

According to a third aspect of the present disclosure there is provided a method for calculating filter coefficients for use in one or more digital fixed infinite impulse response filters of an active noise cancellation controller, each digital fixed infinite impulse response filter being a filter of a predetermined order, the method comprising the steps of: modeling the active noise cancellation controller as a control system in a numerical computing environment, each of the one or more digital fixed infinite impulse response filters of the active noise cancellation controller being replaced with a respective adaptive finite impulse response filter; providing a simulated noise signal to the model of the active noise cancellation controller, the simulated noise signal being representative of the environmental noise experienced by the active noise cancellation controller in use; operating the model of the active noise cancellation controller on the simulated noise signal so as to cause the filter coefficients of the one or more adaptive finite impulse response filters to each converge on a set of first optimum filter coefficients; and converting each set of first optimum filter coefficients into a set of filter coefficients for the respective fixed infinite impulse response filter in dependence on the predetermined order of the respective fixed infinite impulse response filter.

Preferably, the method further comprises: prior to converting each set of first optimum filter coefficients into a set of filter coefficients for the respective fixed infinite impulse response filter, converting each set of first optimum filter coefficients into a set of filter coefficients for an adaptive infinite impulse response filter; replacing each of the one or more adaptive finite impulse response filters in the model of the active noise cancellation controller with a respective adaptive infinite impulse response filter; operating the model of the active noise cancellation controller on the simulated noise signal so as to cause the filter coefficients of the one or more adaptive infinite impulse response filters to each converge on a set of second optimum filter coefficients; and converting each set of second optimum filter coefficients into a set of filter coefficients for the respective fixed infinite impulse response filter in dependence on the predetermined order of the respective fixed infinite impulse response filter.

Preferably, the simulated noise signal includes both broadband and periodic signals. Preferably, the adaptive finite impulse response filters and the adaptive infinite impulse response filters are configured to operate in accordance with one of the following adaptive algorithms: a Least Mean Squares algorithm and a Recursive Least Squares algorithm.

BRIEF DESCRIPTION OF THE DRAWINGS

The present disclosure will now be described by way of example with reference to the accompanying drawings, in which.

DETAILED DESCRIPTION

The following description is presented to enable any person skilled in the art to make and use the disclosure, and is provided in the context of a particular application. Various modifications to the disclosed embodiments will be readily apparent to those skilled in the art.

The general principles defined herein may be applied to other embodiments and applications without departing from the spirit and scope of the present disclosure. Thus, the present disclosure is not intended to be limited to the embodiments shown, but is to be accorded the widest scope consistent with the principles and features disclosed herein.

The present disclosure relates to an active noise cancellation (ANC) controller. The novel ANC controllers described herein may be employed in any device, vehicle or structure in which noise cancellation may be required or advantageous and are not limited to use in headphones, wireless or otherwise. For example, an ANC controller configured in accordance with the present disclosure could be arranged for use in aircraft, automobiles, submarines, or in any other vehicle, building or space so as control the noise level experienced by the occupants by means of one or more loudspeakers configured to generate an "anti-noise" signal.

Figure 10:
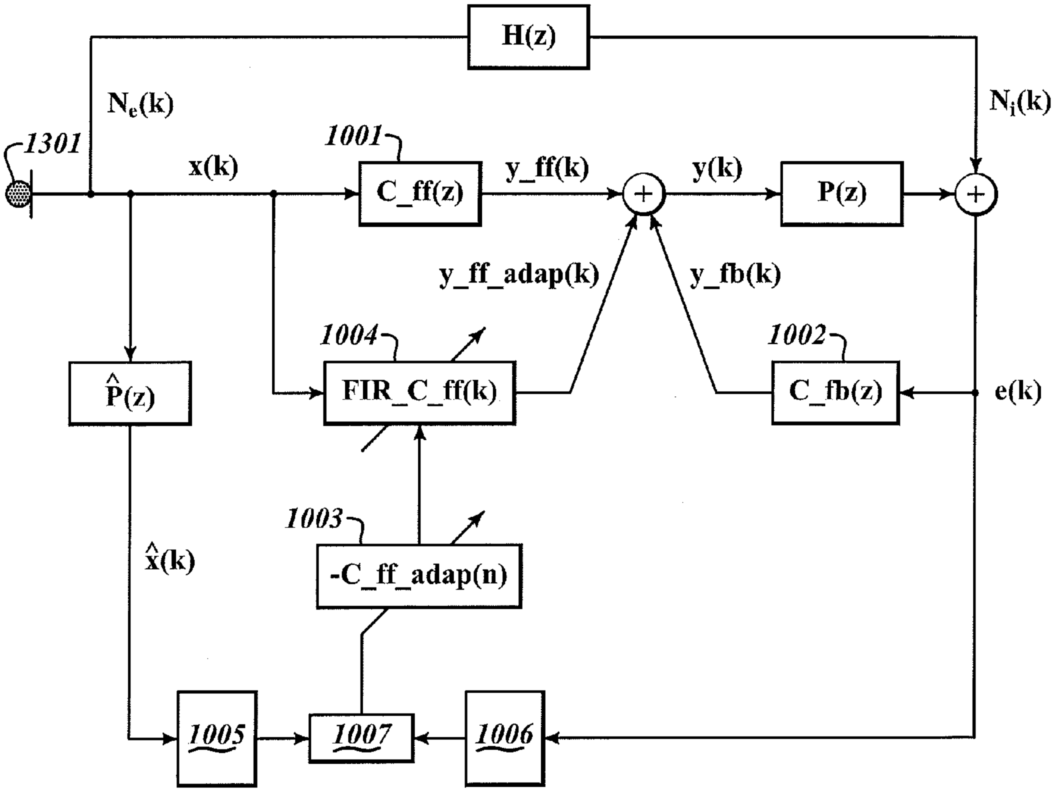
FIG. 10 is a block diagram of a control system representing a combined fixed hybrid feedforward-feedback controller and adaptive feedforward controller configured in accordance with the present disclosure.

A block diagram of a control system representing an ANC controller configured in accordance with the general principles of the present disclosure is shown in FIG. 10. The aggregate ANC controller shown in the figure employs a fixed feedforward controller C_ff(z) 1001, a fixed feedback controller C_fb(z) 1002 and an adaptive feedforward controller FIR_C_ff(k) 1004. C_ff(z) and C_fb(z) are arranged so as to form a fixed hybrid feedforward-feedback controller for the attenuation of broadband noise, and FIR_C_ff(k) is arranged so as to attenuate periodic or tonal signals. The filters are preferably digital filters.

The controllers 1001, 1002 of the hybrid feedforward-feedback controller are infinite impulse response (IIR) filters, for example, digital $4^{th}$-order IIR filters. The adaptive feedforward controller 1004 is a fixed impulse response (FIR) filter whose coefficients are determined in accordance with a subband adaptive algorithm as described below. The outputs from the three controllers y_ff(k), y_fb(k) and y_ff_adap(k) (from the fixed IIR feedforward filter, the fixed IIR feedback filter, and the adaptive feedforward FIR filter, respectively) are combined to form aggregate controller output y(k).

The coefficients of the adaptive feedforward controller are determined in accordance with a subband adaptive algorithm 1007. Preferably the algorithm is an FXLMS algorithm, although it could be any suitable algorithm known in the art. Blocks 1005 and 1006 are DFT (Discrete Fourier Transform) filter banks configured to operate on a predetermined set of frequency subbands of the time-varying signals $\hat{x}(k)$ and e(k), respectively. Each DFT filter bank generates a set of frequency representations of the respective time-varying signal, one representation for each subband. The subband adaptive algorithm 1007 operates independently on each subband so as to generate a set of coefficients for FIR filter 1004 that minimize the error signal in each subband. For example, if an FXLMS algorithm is being used, the subband adaptive algorithm generates a set of coefficients that minimize the mean squares error (MSE) in each subband.

Since subband adaptive algorithm 1007 generates a set of coefficients expressed in the frequency domain and FIR filter 1004 operates using a set of coefficients expressed in the time-domain, coefficient translator 1003 is configured to translate the coefficients generated by subband adaptive algorithm 1007 into a set of coefficients suitable for FIR filter 1004 and map those coefficients into filter 1004. In this manner, when FIR filter 1004 operates on signal x(k), it acts to minimize the error in each subband defined by DFTs 1005 and 1006.

The bandwidth of each subband is preferably substantially less than the total bandwidth of the signals that are to be noise-cancelled. For example, for an ANC controller configured to provide noise cancellation over the frequency range 20-1000 Hz (which might be suitable for a pair of noise-attenuation headphones that can operate over a total bandwidth of 20 Hz-20 kHz) the width of the subbands would preferably be around 25 Hz. For a signal having a sample rate of 48 kHz and for a target subband width of around 25 Hz, a DFT filter bank with 2048 subbands is necessary.

By minimizing the error on a subband basis, the present disclosure avoids the poor signal attenuation that can occur at particular frequencies when an adaptive filter algorithm is configured to minimize the full-band error. This disclosure recognizes that, by simply minimizing the full-band error, the error within certain subbands can actually increase when the full-band error is minimized.

The present disclosure combines both a fixed hybrid feedforward-feedback controller with an adaptive feedforward controller implemented as a subband adaptive filter. This allows the effective cancellation of both broadband and period noise even when the ANC adaptive controller is implemented at processors that are not optimized for noise attenuation algorithms and present a significant delay on the digital path. An adaptive digital feedforward controller is preferably used instead of an adaptive digital feedback controller because the latter generally exhibits poor attenuation of broadband noise when there is a significant delay on the digital path. Adaptive digital feedforward controllers do not typically suffer from such poor performance with respect to broadband noise and are relatively more robust. However, in the particular example of ANC headphones, because the internal and external microphones are close together it should be noted that a short delay is maintained on the controller path so as to achieve acceptable broadband noise attenuation at both controllers of the hybrid controller. In less preferred embodiments of the present disclosure the adaptive digital feedforward controller could be replaced with an adaptive digital feedback controller also implemented as a subband adaptive filter.

It is advantageous if the coefficients of the IIR filters 1001 and 1002 are determined in accordance with the following method:

1. Model the hybrid feedforward-feedback controller using adaptive FIR filters in place of the fixed IIR filters, the FIR filters being configured to minimise the full-band error in a simulated noise signal in accordance with the FXLMS algorithm. The noise signal preferably includes both broadband and periodic signals so as to reflect the environment in which the ANC controller is likely to be used. For example, for a pair of headphones the simulated noise signal could be a recording of aircraft cabin noise—this is provided as reference signal x(k) and error signal e(k).
2. Allow the coefficients of the FIR filters to converge, i.e. to approach values that minimise the error signal representing the noise that is not cancelled by the active noise cancellation controller and remains at microphone 1302.

3. Transform the adaptive FIR filters into fixed IIR filters of the desired filter order using the coefficients determined for the FIR filters.

Step 3 can be, for example, performed in MATLAB using the following functions:

$[h,w]$=freqz(FIRb,1,FFT size)

$$[b,a]=\text{invfreqz}(h,w,b\text{Order},a\text{Order})$$

where F/Rb is a vector representing the polynomial coefficients of the transfer function of the FIR filter (the denominator of an FIR filter is 1) and h and w are frequency response and angular frequency vectors, respectively, of the FIR filter. The invfreqz function then yields the numerator and denominator polynomial coefficients b and a, respectively, for the IIR filter for the chosen orders for the numerator and denominator polynomials, bOrder and aOrder. The IIR filter is therefore represented by the vectors b/a. Preferably the IIR filters are fourth-order IIR filters and the parameters bOrder and aOrder are selected so as to cause fourth-order filter parameters to be generated.

In order to further improve the performance of the fixed IIR filters, the coefficients of the IIR filters can be refined using an adaptive IIR algorithm:

4. Model the hybrid feedforward-feedback controller using adaptive IIR filters in place of the fixed IIR filters, the initial values for the coefficients of the IIR filters being those obtained from the FIR to IIR filter transformation at step 3. As is well known in the art, adaptive algorithms for the adaptive IIR filters are selected according to the characteristics of the system in which the filter is being used. For example, the adaptive algorithms could be least mean squares (LMS) or recursive least squares (RLS) algorithms. Several different adaptive algorithms and their uses are described in Section 9.5.1 of "Adaptive Filtering: Algorithms and Practical Implementation" by P. S. R. Diniz, Prentice Hall and in U.S. patent application Ser. No. 200//0310645.
5. Allow the coefficients of the IIR filters to converge and use these refined coefficients as the coefficients of the fixed IIR filters.

The modeling method set out above can be performed in a numerical computing environment, such as MATLAB.

Figure 11:
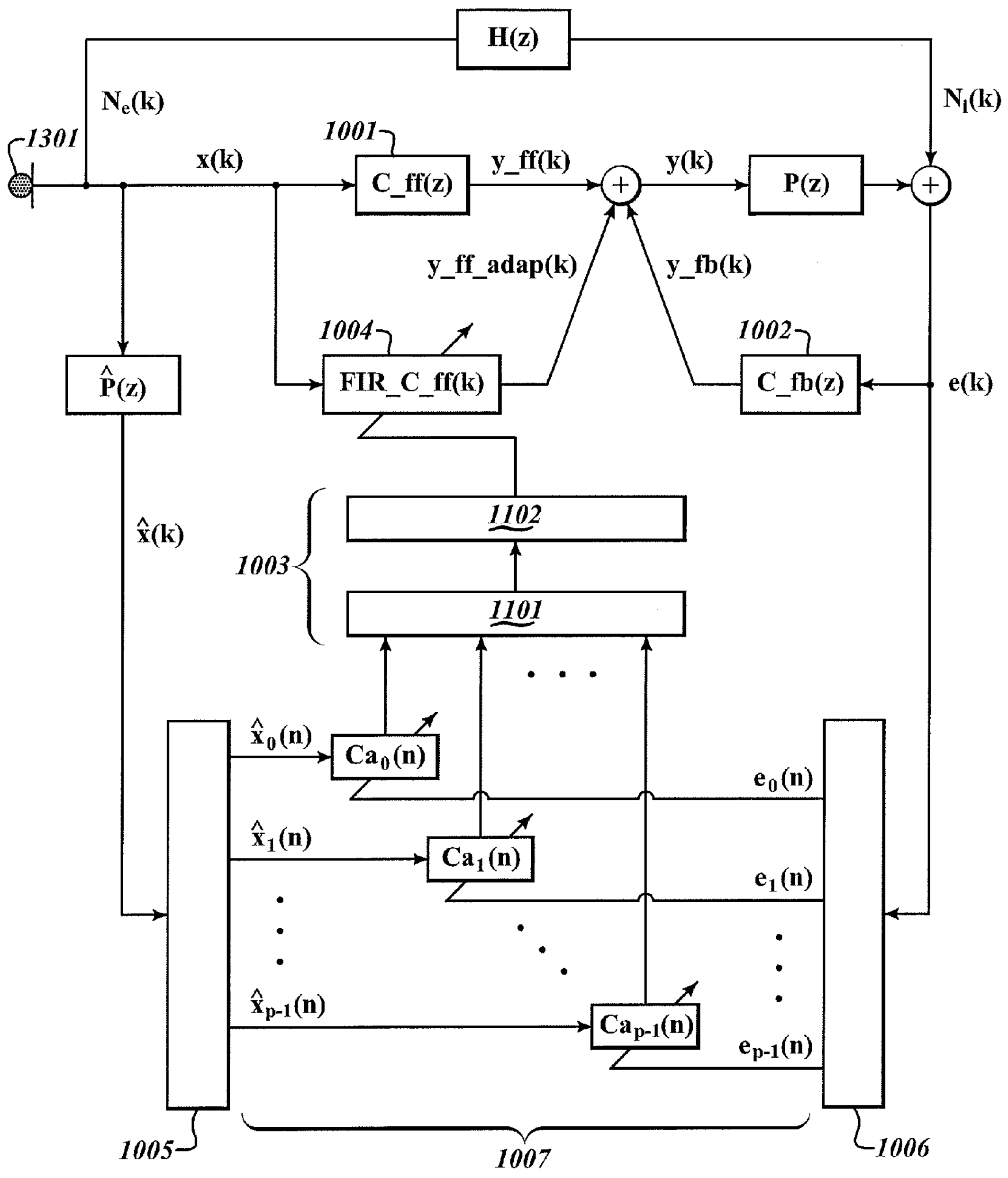
FIG. 11 is a block diagram of a control system representing an ANC controller configured in accordance with preferred embodiments of the present disclosure.

A block diagram of a control system representing an ANC controller configured in accordance with the present disclosure and having a preferred subband adaptive feedforward controller arrangement is shown in FIG. 11. The subband adaptive feedforward controller arrangement comprises controller 1004, coefficient translator 1003, subband adaptive algorithm 1007, and DFTs 1005 and 1006. The figure shows the subband adaptive algorithm in an expanded view so as to illustrate the subband filter coefficients $Ca_i(n)$ determined for each subband by the algorithm. The figure also shows that coefficient translator 1003 comprises coefficient mapping algorithm 1101 and inverse FFT (Fast Fourier Transform) 1102.

The coefficients $Ca_i(n)$ generated by the subband adaptive algorithm 1007 are updated according to the following equation:

$$Ca_i(n+1)=Ca_i(n)+\mu_i(n)[\hat{X}_i^*(n)e_i(n)]$$

where $Ca_i(n)$ is a column vector with R coefficients of the i-th FIR subband adaptive filter; $\hat{X}_i(n)$ is a column vector holding the last R samples of $\hat{x}i_i(n)$ generated by DFT filter bank 1005; $\mu_i(n)$ is the step size of the i-th subband adaptive filter; and '*' represents the conjugate value of $X_i(n)$. Due to the use of the DFT filter banks 1005 and 1006, $\hat{x}_i(n)$, $e_i(n)$ and $Ca_i(n)$ are complex values. In order to obtain the full band adaptive filter 1004, it is necessary to perform an inverse Fourier transform on the set of coefficients $Ca_i(n)$.

In order to determine which subband filter coefficients $Ca_i(n)$ should be mapped to obtain the filter 1004, the error signal $e_i'(k)$ achieved by the hybrid feedforward-feedback filters 1001 and 1002 alone must be determined. This is because the coefficients $Ca_i(n)$ are only mapped into filter 1004 if they provide an improvement in noise attenuation; coefficients that do not improve noise attenuation are not used. In order to determine whether there is an improvement in noise attenuation due to the adaptive filter, the error provided by the hybrid controller alone $e_i'(k)$ has to be estimated and compared with $e_i(k)$, which is the net error signal due to all the filters.

The error signal $e_i'(k)$ can be calculated if the transfer function between the two microphones $\hat{H}(z)$ 1201 of the physical system is known. Once the transfer function 1201 between the internal 1302 and external 1301 microphone has been measured, the control theory representation of the ANC controller in FIG. 12 tells us that the error estimates $e_i'(n)$ are given by the output of DFT filter bank 1006. In other words, by modeling the control system shown in FIG. 12 when transfer function 1201, the plant function and the coefficients of the fixed IIR filters are known, the subband error estimates $e_i'(n)$ can be calculated. Note that $\hat{P}(z)$ shown in the figures is the Z-transform of the plant impulse response P(n).

Figure 12:
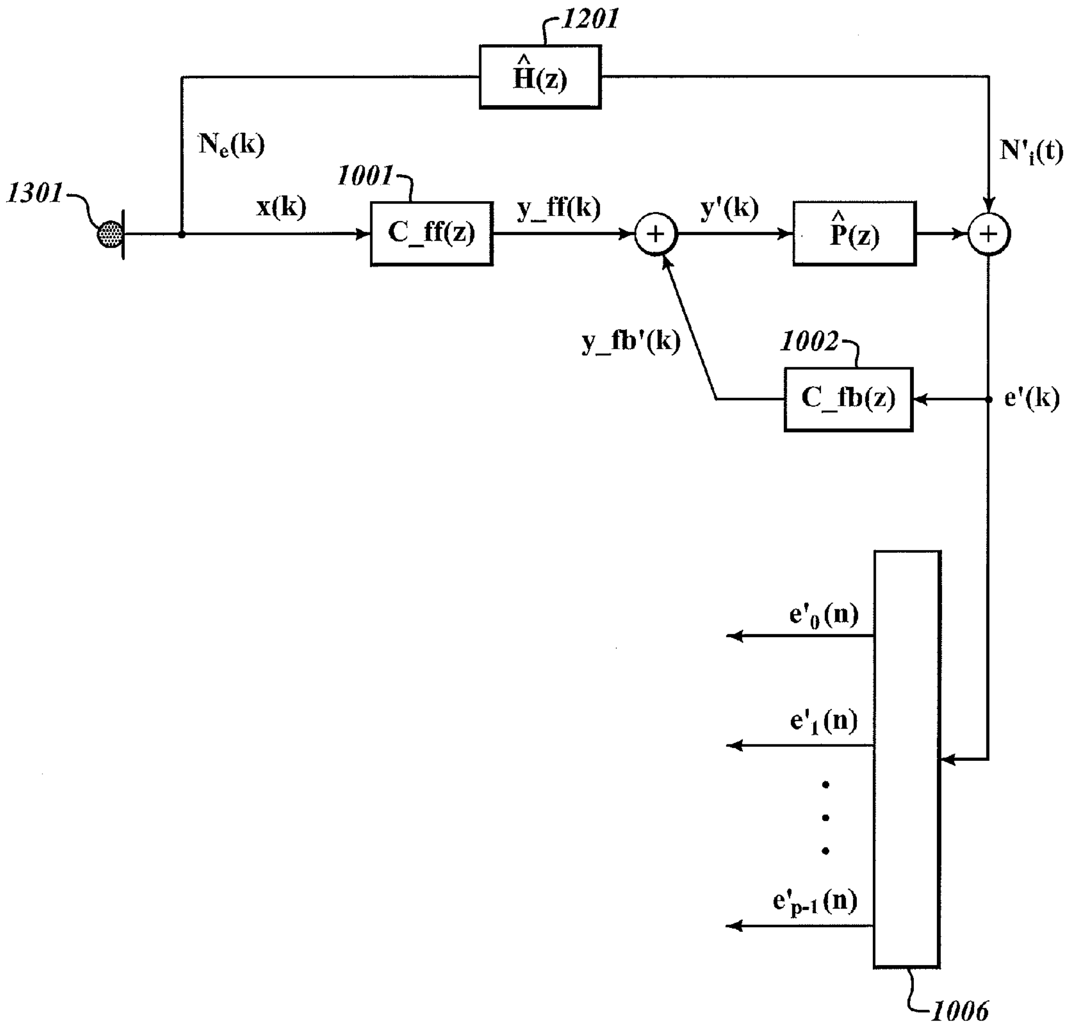
FIG. 12 is a block diagram illustrating a control system configured to estimate the error signal for the subbands of the adaptive feedforward filter.

In preferred embodiments of the present disclosure, the adaptive feedforward controller is configured to form an estimate of the error in each subband due to the hybrid feedforward-feedback controller alone in accordance with the control theory representation in FIG. 12 and using the input signal from the external microphone, $n_e(k)$. In other words, the adaptive controller calculates error estimates $e'_i(k)$ from input $n_e(k)$ according to a stored transfer function $\hat{H}(z)$, a stored plant function $\hat{P}(z)$, and the known filter coefficients of the hybrid controller. Such calculations could be performed at a DSP (digital signal processor) of the ANC controller.

In order to maximize noise attenuation and to avoid instability of the system due to divergence of the subband adaptive filters, it is advantageous if the following coefficient mapping algorithm is used based on a comparison of the measured error $e_i(k)$ and the estimated hybrid error $e'_i(k)$ in each subband. For each subband is 1. if the net error in the subband $e_i(n)$ is smaller than the estimated error in the subband $e'_i(n)$ that is achieved by the hybrid feedforward-feedback controller alone, map the respective coefficients $Ca_i(n)$ into FIR filter FIR_C_ff(k);
2. otherwise, set the coefficients $Ca_i(n)$ of the digital filter for that subband to zero.

Figure 1:
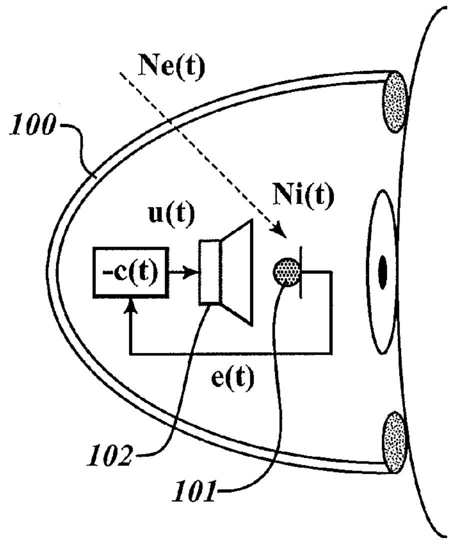
FIG. 1 is a schematic diagram of an ambient noise reduction headphone.
Figure 2:
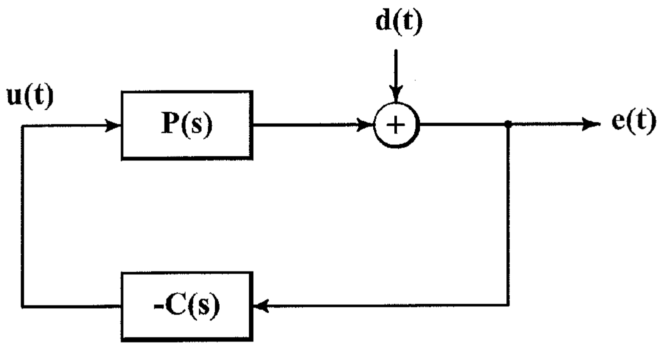
FIG. 2 is a block diagram of the disturbance rejection problem.
Figure 3A:
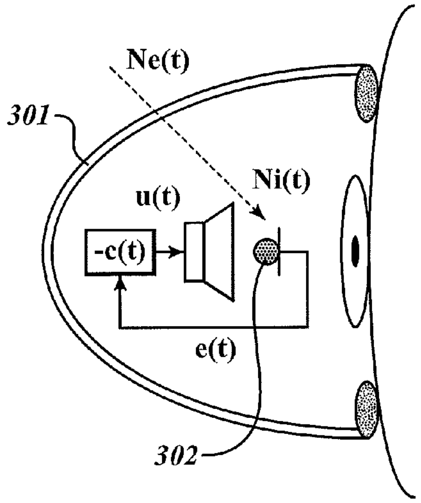
FIG. 3A is a schematic diagram of an ambient noise reduction headphone having a feedback arrangement.
Figure 3B:
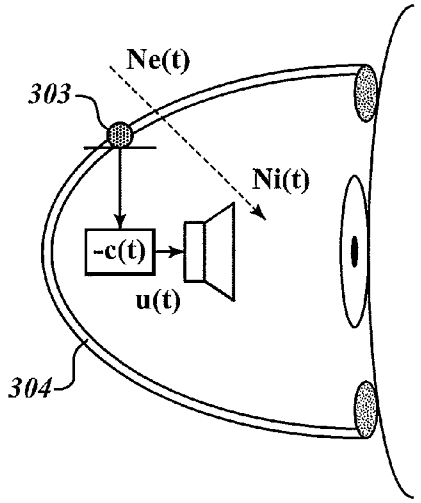
FIG. 3B is a schematic diagram of an ambient noise reduction headphone having a feedforward arrangement.
Figure 4:
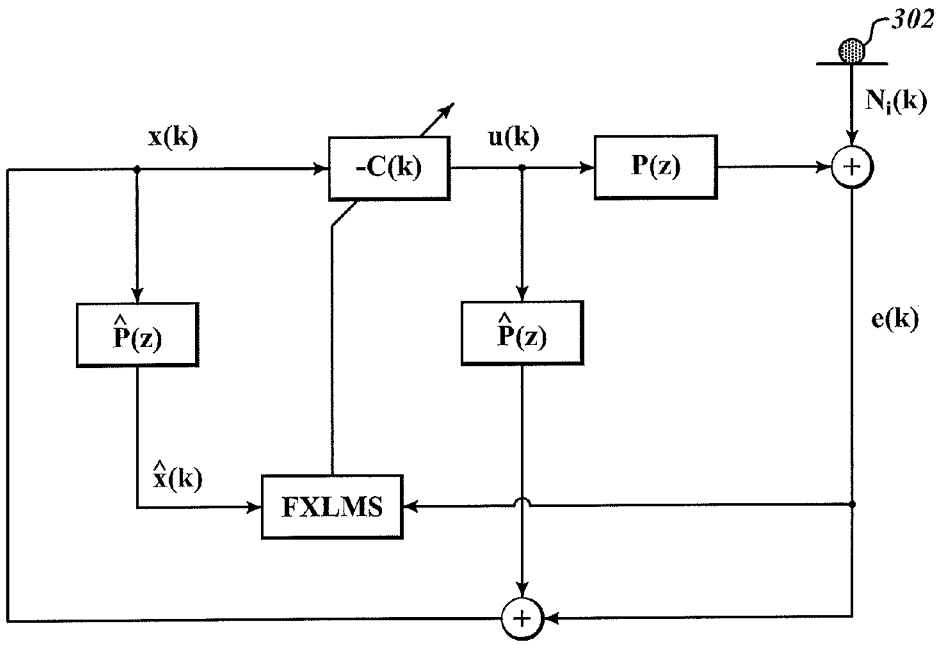
FIG. 4 is a block diagram of a control system representing an adaptive feedback controller for the headphone of FIG. 3A.
Figure 5:
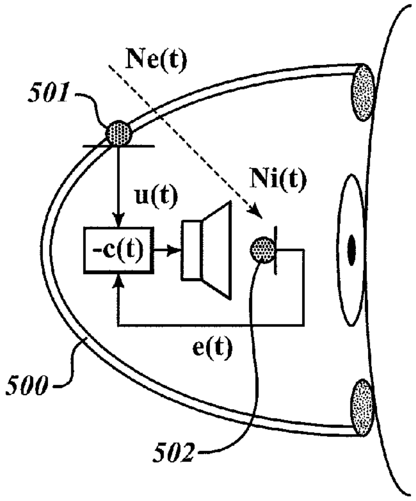
FIG. 5 is a schematic diagram of a practical ambient noise reduction headphone having a feedforward arrangement.
Figure 6:
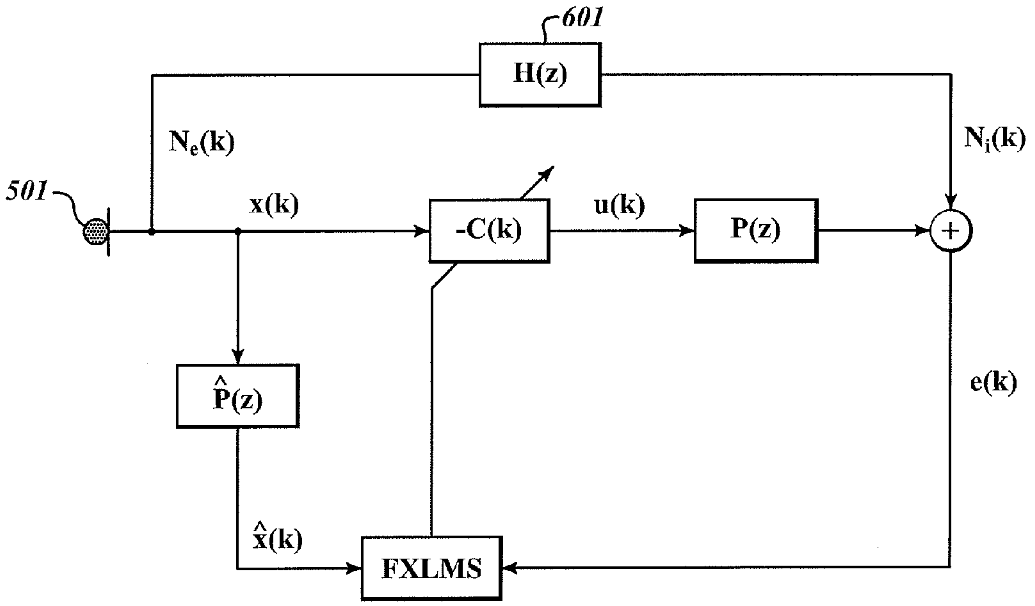
FIG. 6 is a block diagram of a control system representing an adaptive feedforward controller for the headphone of FIG. 5.
Figure 7:
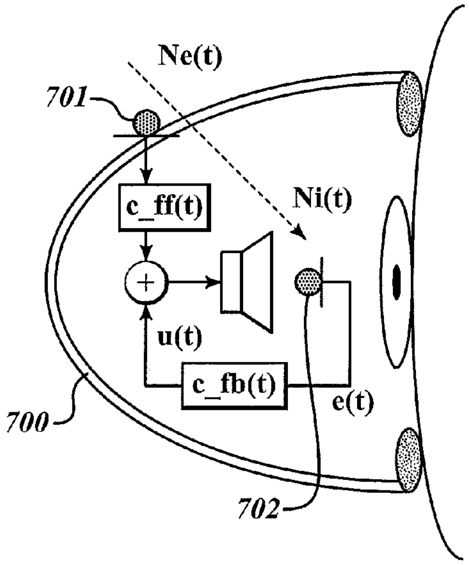
FIG. 7 is a schematic diagram of an ambient noise reduction headphone having a hybrid feedforward-feedback arrangement.
Figure 8:
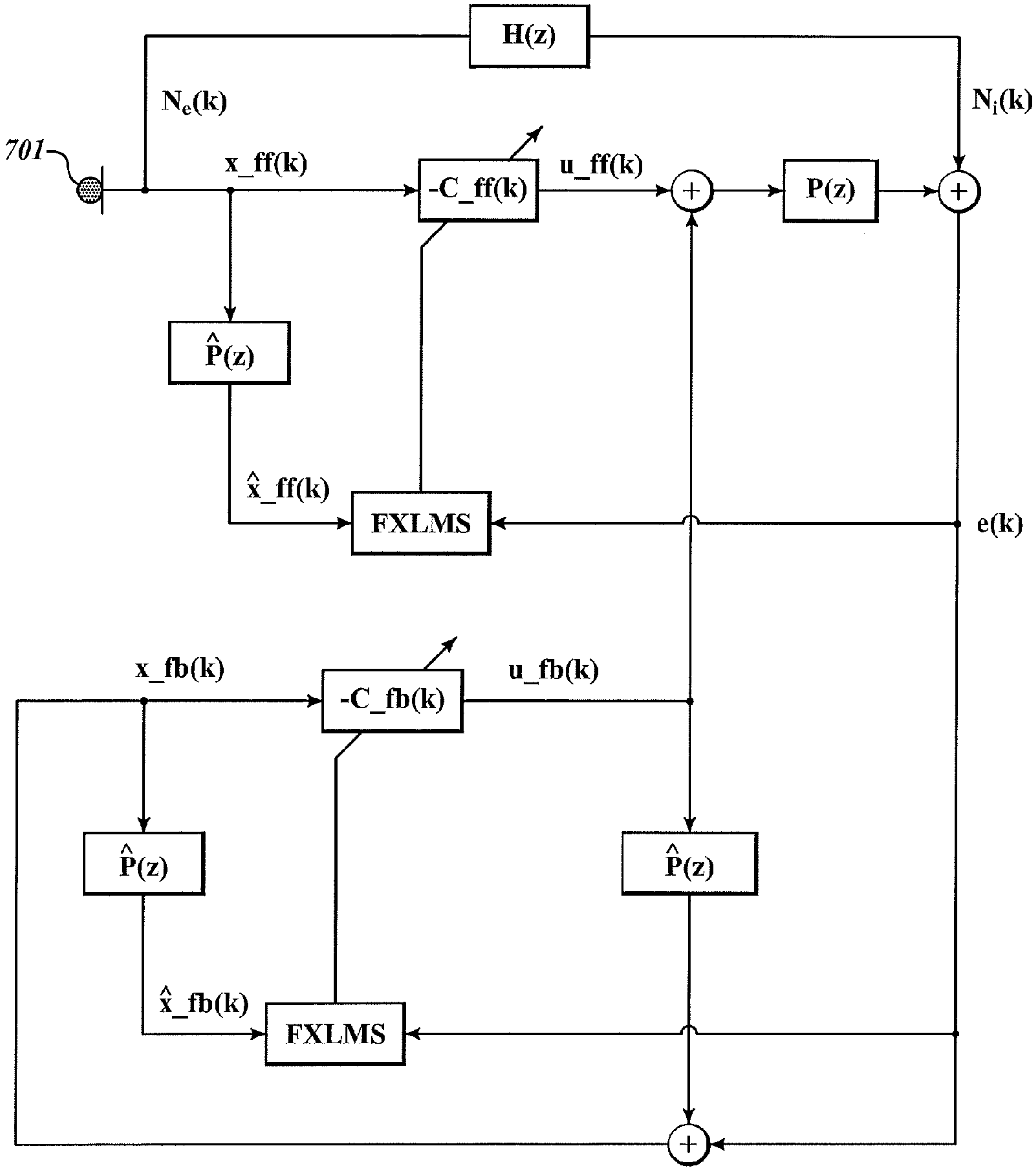
FIG. 8 is a block diagram of a control system representing an adaptive hybrid feedforward-feedback controller for the headphone of FIG. 7.
Figure 9:
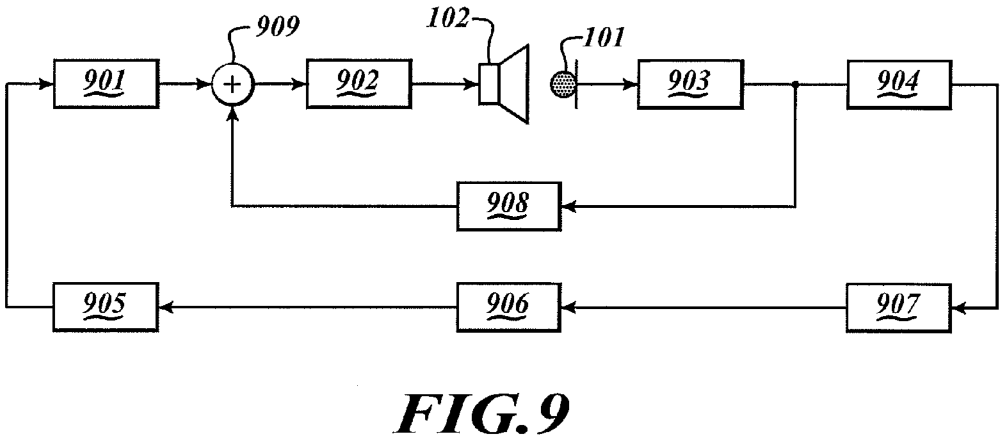
FIG. 9 is a block diagram of the general structure of a hybrid analog-digital controller.
Figure 13:
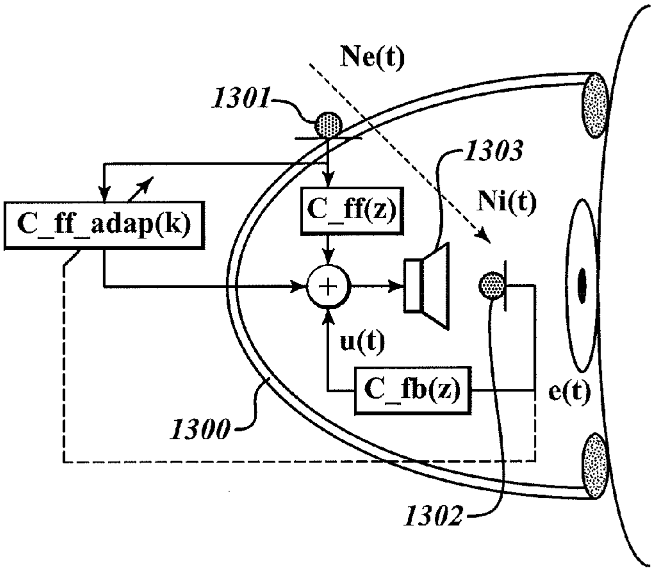
FIG. 13 is a schematic diagram of a headphone implementing an ANC controller configured in accordance with the present disclosure.

An ANC controller configured in accordance with the present disclosure could be implemented at a pair of headphones so as to attenuate the level of environmental acoustic noise perceived by a user of the headphones. A schematic diagram of one-half of a pair of headphones arranged to include an ANC controller of the present disclosure is shown in FIG. 13. The figure shows the basic relationship between the inputs from the internal and external microphones 1302, 1301, the output from the speaker 1303, and the three digital filters C_ff_adap(k), C_ff(z) and C_fb(z) of the ANC controller. The headphones include two microphones arranged in the manner shown in FIG. 5, with one internal microphone 1302 within each headphone cup 1300 and an external microphone 1301 mounted on the exterior of each headphone cup.

Figure 14:
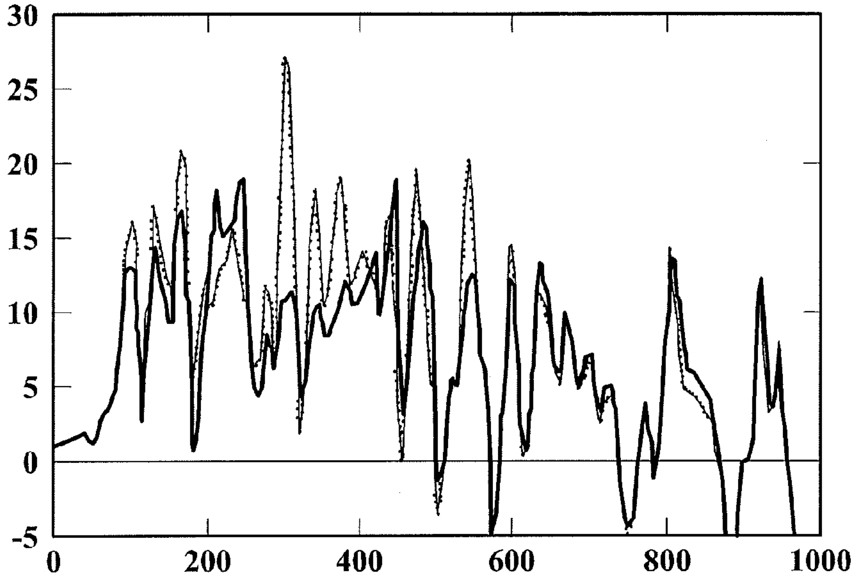
FIG. 14 shows the noise attenuation performance in dB of a simulated ANC controller configured as set out in FIG. 11.

The control system shown in FIG. 11 that represents the preferred embodiment of the present disclosure was simulated in MATLAB and the results of its operation on a reference noise signal are shown in FIG. 14, along with the equivalent performance of the hybrid feedforward-feedback controller alone. The noise signal $n_e(k)$ or x(k) provided to the simulation was in the form of a recording of aircraft cabin noise combined with a 300 Hz sine wave. The coefficients of the fixed IIR filters of the hybrid feedforward-feedback controller were determined in accordance with the method described above, and the adaptive feedforward controller was configured to operate in accordance with the coefficient mapping algorithm describe above once the subband error estimates $e_i'(n)$ due to the hybrid feedforward-feedback controller had been determined in accordance with FIG. 12.

FIG. 14 shows the level of noise attenuation in dB over the frequency range 0-1000 Hz of the hybrid controller with fixed IIR filters alone (solid line) and the ANC controller of the present disclosure comprising a hybrid controller with fixed IIR filters and an adaptive feedforward controller (dotted line) comprising an adaptive FIR filter. Notice that the ANC controller of the present disclosure is much better (by approximately 15 dB) at rejecting the 300 Hz periodic noise signal than the hybrid controller alone, and in terms of broadband noise is at least equal to the noise rejection performance of the hybrid controller alone.

Figure 15:
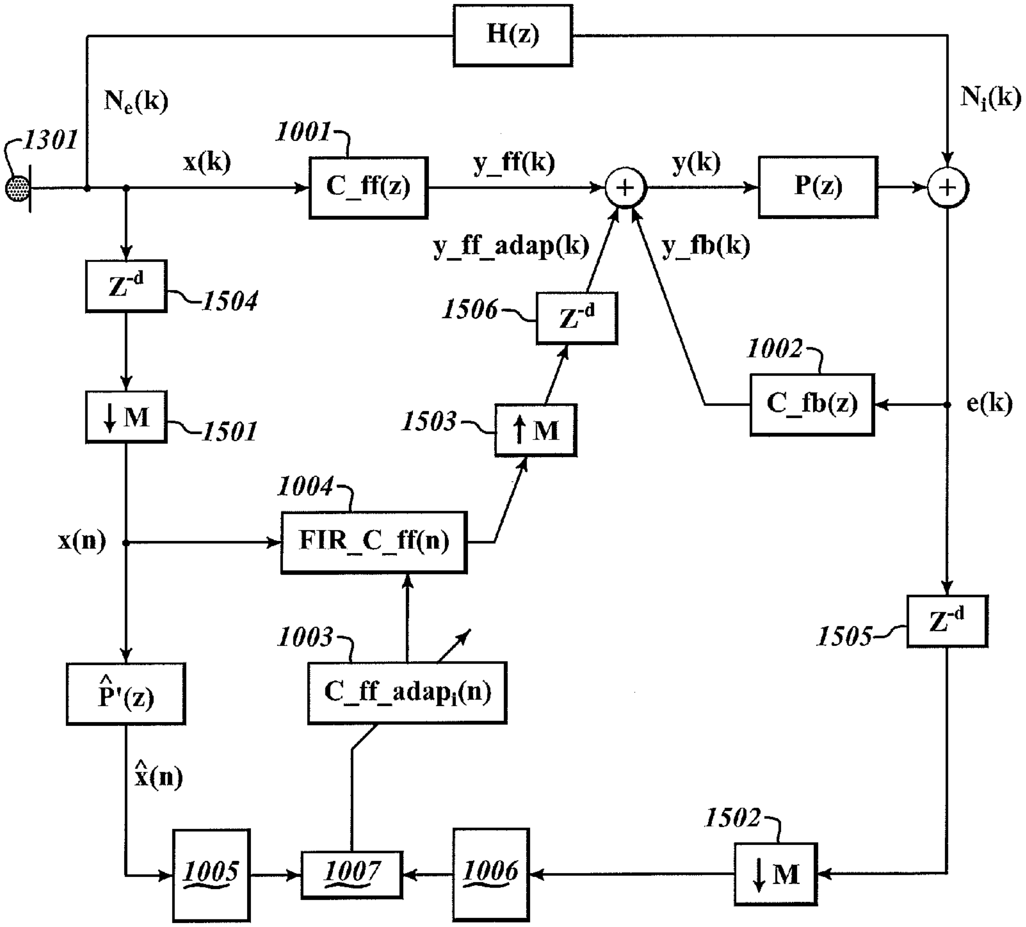
FIG. 15 is a block diagram of a control system representing an ANC controller configured in accordance with the most preferred embodiments of the present disclosure.

The present disclosure can be implemented at low power processors, such as communications controllers, because a digital ANC controller configured in accordance with the present disclosure is robust in the presence of delays and the computational complexity and memory requirements of the adaptive feedforward controller can be readily adapted to the processing power available. In order to reduce the computational complexity of the ANC controller, it is advantageous to apply a decimation factor M so as to reduce the effective sampling frequency of the microphone signals applied to DFTs 1005 and 1006. This allows the FFT of the subband adaptive feedforward controller to be M times smaller yet maintain the same bandwidth. FIG. 15 shows a control system representing the ANC controller of FIG. 11 implemented so as to apply a decimation factor 1501, 1502 to the inputs of the subband adaptive feedforward controller. Following application of the subband adaptive filter 1004 to the reference signal x(n), the decimation is reversed at 1503 so as to restore the original sampling frequency of the reference signal and allow the outputs from filters 1001, 1002 and 1004 to be combined.

Most preferably the decimation factor M is 12 such that a microphone signal that is sampled at 48 kHz is reduced to an effective sampling frequency of 4 kHz. This allows the adaptive feedforward controller to attenuate periodic signals up to 2 kHz which provides good performance for a pair of headphones. However, the decimation factor could be higher so as to further reduce the computational complexity and memory requirements of the subband adaptive filters, but this leads to a corresponding reduction in the maximum periodic frequency that the adaptive feedforward controller could attenuate. For example, if M were 24, the adaptive feedforward controller could only attenuate periodic signals up to a frequency of 1 kHz.

Figure 16:
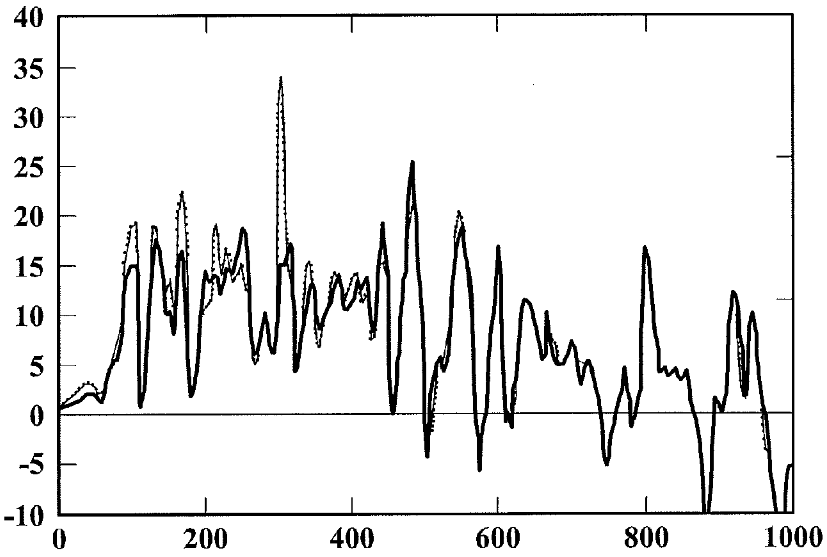
FIG. 16 shows the noise attenuation performance in dB of a simulated ANC controller configured as set out in FIG. 15.

The control system shown in FIG. 15, representing an ANC controller configured in accordance with the present disclosure, was simulated in MATLAB and the results are shown in FIG. 16, along with the equivalent performance of the hybrid feedforward-feedback controller alone. The noise signal $n_e(k)$ or x(k) provided to the simulation was in the form of a recording of aircraft cabin noise combined with a 300 Hz sine wave. The coefficients of the fixed IIR filters of the hybrid feedforward-feedback controller were determined in accordance with the method previously described, and the adaptive feedforward controller was configured to operate in accordance with the coefficient mapping algorithm describe above once the subband error estimates $e_i'(n)$ due to the hybrid feedforward-feedback controller had been determined in accordance with FIG. 12.

In order to simulate the real-world operation of the ANC controller at a processor that might not be optimized for performing digital active noise attenuation, a delay of 2.5 ms (represented by blocks 1504 and 1505 in FIG. 15) was introduced into the input paths and output path (block 1506) of the adaptive feedforward controller (for a total delay of 5 ms). This replicates the delay that might be present on the digital path of a processor at which the present disclosure could be implemented.

FIG. 16 shows the level of noise attenuation in dB over the frequency range 0-1000 Hz of the hybrid controller with fixed IIR filters alone (solid line), and the ANC controller of the present disclosure comprising a hybrid controller with fixed IIR filters and an adaptive feedforward controller (dotted line) comprising an adaptive FIR filter. It can be seen that the low complexity implementation of the present disclosure still achieves the desired improvement in the attenuation of periodic signals (the plot of the complete ANC controller includes an attenuation spike at 300 Hz) and matches or exceeds the broadband noise rejection of the hybrid controller alone.

Figure 17:
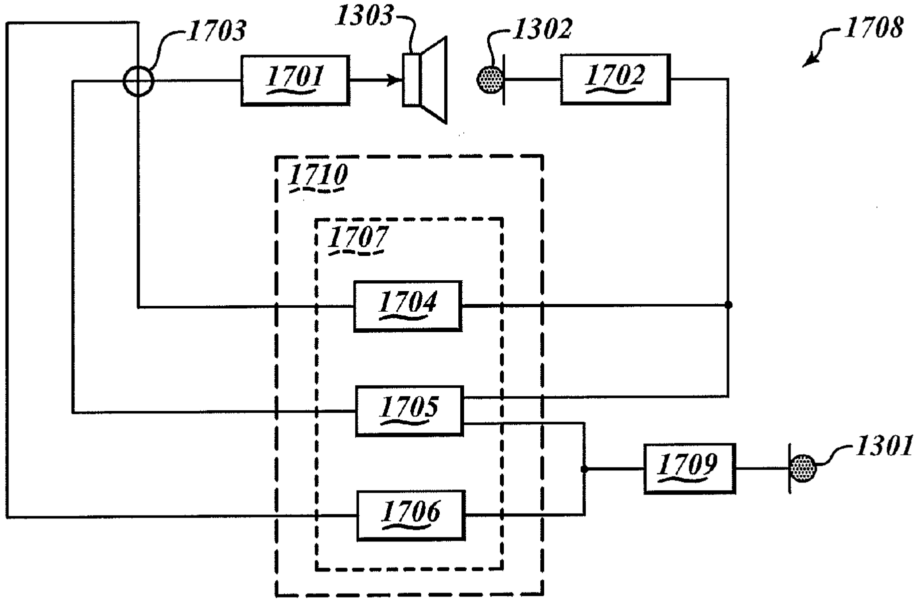
FIG. 17 is a schematic diagram of an ANC controller configured in accordance with the present disclosure.

An ANC controller configured in accordance with the present disclosure is shown in FIG. 17, arranged within an active noise attenuation system 1708 including a loudspeaker 1303, microphones 1301, 1302 and a digital processor 1710. The controller requires two microphones 1302 and 1301: microphone 1302 is positioned close to loudspeaker 1303 so as to provide an error signal e(k) at its output indicative of the error in the cancellation of environmental noise by the loudspeaker; microphone 1301 is positioned away from loudspeaker 1303 so as to provide a reference signal $n_e(k)$ at its output indicative of the noise in the environment of the ANC controller. The ANC controller could be located at a pair of headphones, in which case the microphones 1301 and 1302 are preferably arranged as shown in FIG. 13. More generally, the ANC controller could be located in any space in which noise cancellation is required, such as a vehicle or room.

Microphone 1301 need not be external to an enclosed space in which noise cancellation is provided but is preferably located substantially further away from the loudspeaker than microphone 1302 and the acoustic output of the loudspeaker is preferably not directed towards microphone 1301. There may be more than one loudspeaker 1303: each could have a corresponding microphone 1302 and the outputs of those microphones being aggregated so as to provide a single error signal; alternatively, there could be one microphone 1302 arranged to provide a single error signal to the ANC controller. In any arrangement, each microphone 1301 or 1302 could be a group of one or more co-located microphones.

Typically, loudspeaker 1303 will be driven by a power amplifier 1701 and the output signals from microphones 1302 and 1301 will be amplified at pre-amplifiers 1702 and 1709, respectively.

The individual controllers 1704, 1705 and 1706 that make up the ANC controller 1707 of the present disclosure are supported at a digital processor 1710. The digital processor could be any kind of processor, including a communications controller (possibly wireless, such as a Bluetooth or WiFi controller), a central processing unit (CPU) of a portable device, and an audio controller of a portable device. The digital processor will typically be an integrated circuit, and could be a System-on-a-Chip (SoC), an ASIC (Application-Specific Integrated Circuit), an FPGA (Field Programmable Gate Array), a microprocessor executing an instruction set stored in an associated memory, or a hardwired processor. How an ANC controller of the present disclosure is implemented at a given processor is a matter of the particular characteristics of that processor and will be readily apparent to a person of skill in the art from the disclosure set out herein.

Generally, digital processor 1710 is a DSP that can be configured provide the hybrid and adaptive filters. The delay in the control path of the processor should be short so as to ensure that the hybrid controller provides adequate performance—typically, the delay should be less than approximately 200 μs for the hybrid controller, and less than 5 ms for the adaptive feedforward controller.

The three controllers that make up ANC controller 1707 are the fixed feedback controller 1704 and the fixed feedforward controller 1706 that together form the hybrid feedforward-feedback controller, and adaptive feedforward controller 1705. Each of these controllers may be physically independent digital units of the processor 1710, but are preferably logical entities defined in the logic of the processor 1710. Thus, there may not be three distinct physical controllers as shown in FIG. 17. Note that the feedback controller takes as its input error microphone 1302; feedforward controller 1706 takes as its input reference microphone 1301; and adaptive feedforward controller 1705 takes both microphones as its inputs. The outputs of the three controllers is combined at aggregator 1703 so as to provide a noise cancellation signal to loudspeaker 1303. In operation, the noise cancellation signal causes the loudspeaker to modulate in such a way as to minimize the environmental noise detected at microphone 1302. Aggregator 1703 preferably sums the signals together; it could additionally perform some signal matching between the outputs of the three controllers.

Note that the controllers identified in FIGS. 10 to 13 and 15 are mathematical representations of aspects of the physical controllers shown in FIG. 17. For example, adaptive feedforward controller 1705 comprises the functions of several of the blocks shown in FIG. 10, including the DFTs 1005 and 1006, the subband adaptive algorithm 1007 and the coefficient mapping algorithm 1003, as well as subband FIR adaptive filter 1004. The functional blocks of the control systems shown in FIGS. 10 to 13 and 15 are merely mathematical representations of ANC controllers configured in accordance with the present disclosure, and are not to be taken to indicate discrete functional parts of a physical ANC controller. It should in particular be understood that the plant functions P(z) and the transfer functions H(z) are not physical components of the ANC controller but, as is well known in the art, are simply mathematical representations describing the relationship between various signals in the control systems.

The ANC controller represented by the control system of FIG. 15 and in accordance with the physical arrangement of FIG. 17 can be implemented at the side tone path of a Bluetooth communications processor that includes $4^{th}$-order IIR filters, a digital-to-analog converter (DAC) path delay of <200 μs at a sample rate of 48 kHz, and a DSP path latency of ~1 ms. The present disclosure allows a Bluetooth controller to provide both Bluetooth communication functions and active noise cancellation in a single integrated circuit. This considerably reduces the bill of materials for manufacturing Bluetooth headphones that provide active noise cancellation.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present disclosure may consist of any such individual feature or combination of features. In view of the foregoing description it will be evident to a person skilled in the art that various modifications may be made within the scope of the disclosure.

The invention claimed is:

1. An active noise cancellation controller for performing noise attenuation in a system over a predetermined frequency range, the active noise cancellation controller comprising:

a first input for receiving a reference signal indicative of a noise level;

a second input for receiving an error signal indicative of a remnant noise level;

an output for providing a noise cancellation signal to a system in which noise attenuation is to be performed;

a fixed feedback controller having a fixed infinite impulse response filter arranged for operation on an error signal received at the second input;

a fixed feedforward controller having a fixed infinite impulse response filter arranged for operation on a reference signal received at the first input; and an adaptive feedforward controller having a digital adaptive finite impulse response filter arranged for operation on a reference signal received at the first input and on an error signal received at the second input, the coefficients of the digital adaptive filter being determined by:

in the frequency domain, independently generating a set of initial coefficients for each of a plurality of subbands into which the predetermined frequency range is divided, said sets of initial coefficients being generated in accordance with a predetermined adaptive algorithm; and transforming said sets of initial coefficients into the time domain for use as the said coefficients of the digital adaptive filter;

wherein the fixed feedback controller, fixed feedforward controller and adaptive feedforward controller are arranged to, in use, provide a noise cancellation signal at the output in dependence on a reference signal received at the first input and an error signal received at the second input.

2. An active noise cancellation controller as claimed in claim 1, wherein the adaptive feedforward controller further comprises:

a first Discrete Fourier Transform unit operable to form a frequency domain representation of a reference signal received at the first input; and a second Discrete Fourier Transform unit operable to form a frequency domain representation of an error signal received at the second input;

wherein the predetermined adaptive algorithm is configured to generate the initial coefficients using frequency domain representations of error and reference signals so formed at the first and second Discrete Fourier Transform units.

3. An active noise cancellation controller as claimed in claim 2, wherein the first and second Discrete Fourier Transform units are configured to, on forming a frequency domain representation, generate a set of parameters for each subband of the predetermined frequency range, the parameters of a subband being frequency domain representations of the error and reference signals in that subband.

4. An active noise cancellation controller as claimed in claim 2, wherein the adaptive feedforward controller further comprises a third Discrete Fourier Transform unit operable to transform initial coefficients generated by the predetermined adaptive algorithm into the time domain for use as the said coefficients of the digital adaptive filter.

5. An active noise cancellation controller as claimed in claim 4, wherein the third Discrete Fourier Transform unit is configured to use an inverse Fast Fourier Transform algorithm.

6. An active noise cancellation controller as claimed in claim 4, wherein the adaptive feedforward controller further comprises a coefficient mapping unit configured to, for each subband:

form an estimate of the magnitude of an error signal at the second input in the subband due to the fixed feedback and fixed feedforward controllers but not due to the adaptive feedforward controller; and if the estimate of the magnitude of the error signal at the second input in the subband is greater than the magnitude of an error signal at the second input due to the fixed feedback and fixed feedforward controllers and the adaptive feedforward controller:

provide the set of initial coefficients of the subband to the third Discrete Fourier Transform unit for conversion into the time domain;

and otherwise:

set the initial coefficients of the subband to zero and provide the zeroed initial coefficients to the third Discrete Fourier Transform unit.

7. An active noise cancellation controller as claimed in claim 6, wherein the adaptive feedforward controller is configured to, for each subband and from a reference signal received at the first input, form said estimate of the magnitude of an error signal at the second input in the subband due to the fixed feedback and fixed feedforward controllers in dependence on, firstly, a stored transfer function that relates a reference signal received at the first input to an error signal received at the second input and, secondly, a stored plant function that relates a combined output of the fixed feedback and fixed feedforward controllers to an error signal received at the second input, the transfer function and plant function being mathematical representations of a physical system in which the active noise cancellation controller is configured to perform noise attenuation.

8. An active noise cancellation controller as claimed in claim 2, further comprising first and second decimation units and an interpolation unit:

the first decimation unit being arranged to operate on a reference signal received at the first input and the second decimation unit being arranged to operate on an error signal received at the second input, the decimation units being configured so as to reduce the effective sampling rate of the respective signals by a predetermined factor and provide the decimated signals to the first and second Discrete Fourier Transform units; and the interpolation unit being arranged to operate on the cancellation signal generated by the adaptive feedforward controller so as to increase the effective sampling rate of the cancellation signal by said predetermined factor.

9. An active noise cancellation controller as claimed in claim 1, wherein the active noise cancellation controller is adapted for use at an audio device such that:

the first input is configured to receive a reference signal from a first microphone, the reference signal being representative of the level of acoustic noise in the environment of the headphones or audio headset;

the second input is configured to receive an error signal from a second microphone, the error signal being representative of the level of acoustic noise remaining at the second microphone as a result of the operation of the active noise cancellation controller; and the output of the active noise cancellation controller is configured to provide a noise cancellation signal to a loudspeaker so as to cause the loudspeaker to perform acoustic noise cancellation at the second microphone.

10. An active noise cancellation controller as claimed in claim 9, wherein the audio device is a pair of headphones or an audio headset.

11. An active noise cancellation controller as claimed in claim 10, wherein the first microphone is located on the exterior of the pair of headphones or audio headset and the second microphone is located substantially between the loudspeaker and an audio port adapted for engagement with a human ear and arranged to, in use, convey acoustic signals generated at the loudspeaker to a human ear so engaged.

12. An active noise cancellation controller as claimed in claim 1, wherein the predetermined adaptive algorithm is a least mean squares (LMS) or recursive least squares (RLS) algorithm, and is preferably a Filtered-Reference Least Mean Squares algorithm.

13. An active noise cancellation controller as claimed in claim 1, wherein the subbands cover collectively in frequency the predetermined frequency range.

14. An active noise cancellation controller as claimed in claim 1, wherein the frequency range of each subband is significantly less than the predetermined frequency range.

15. An active noise cancellation controller as claimed in claim 14, wherein the frequency range of each subband is at least one order of magnitude less than the predetermined frequency range, and is preferably 40 times less than the predetermined frequency range.

16. An active noise cancellation controller as claimed in claim 15, wherein the predetermined frequency range is approximately 1000 Hz and the frequency range of each subband is approximately 25 Hz.

17. An active noise cancellation controller as claimed in claim 1, wherein adjacent subbands do not overlap in frequency.

18. An active noise cancellation controller as claimed in claim 1, wherein the fixed infinite impulse response filters of the fixed feedback controller and the fixed feedforward controller are digital filters.

19. An integrated circuit comprising a wireless communications controller and an active noise cancellation controller as claimed in claim 1.

20. An integrated circuit as claimed in claim 19, wherein the wireless communications controller is a Bluetooth controller.

* * * * *